(12) United States Patent
Dysarz

(10) Patent No.: US 6,712,787 B1
(45) Date of Patent: *Mar. 30, 2004

(54) SELF DESTRUCTIVE SAFETY SYRINGE

(76) Inventor: Edward D. Dysarz, 18 Front St., Rockport, TX (US) 78382

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/574,017

(22) Filed: May 19, 2000

(51) Int. Cl.⁷ ................................................. A61M 5/00
(52) U.S. Cl. ...................................... 604/110; 128/919
(58) Field of Search ................................ 604/110, 187, 604/195, 197, 218, 220, 222, 227, 239, 198; 128/919

(56) References Cited

U.S. PATENT DOCUMENTS

| | | |
|---|---|---|
| 3,008,570 A | 11/1961 | Roehr et al. |
| 3,107,785 A | 10/1963 | Roehr et al. |
| 3,306,290 A | 2/1967 | Weltman |
| 3,306,291 A | 2/1967 | Burke et al. |
| 3,895,633 A | 7/1975 | Bartner et al. |
| 4,300,678 A | 11/1981 | Gyure et al. |
| 4,356,822 A | 11/1982 | Winstead-Hall |
| 4,392,859 A | 7/1983 | Dent |
| 4,425,120 A | 1/1984 | Sampson et al. |
| 4,639,249 A | 1/1987 | Larson |
| 4,655,751 A | 4/1987 | Harbaugh |
| 4,664,654 A | 5/1987 | Strauss |
| 4,838,863 A | 6/1989 | Allard et al. |
| 4,894,055 A | 1/1990 | Sudnak |
| 4,946,446 A | 8/1990 | Vadher |
| 4,973,316 A | 11/1990 | Dysarz |
| 4,978,343 A | 12/1990 | Dysarz |
| 5,019,044 A | 5/1991 | Tsao |
| 5,084,018 A | 1/1992 | Tsao |
| 5,088,986 A | 2/1992 | Nusbaum |
| 5,120,310 A | 6/1992 | Shaw |
| 5,180,369 A | 1/1993 | Dysarz |
| 5,201,710 A | * 4/1993 | Caselli ..................... 604/110 |
| 5,246,428 A | 9/1993 | Falknor |
| 5,267,961 A | 12/1993 | Shaw |
| 5,385,551 A | 1/1995 | Shaw |
| 5,389,076 A | 2/1995 | Shaw |
| 5,405,376 A | 4/1995 | Mulier et al. |
| 5,407,436 A | 4/1995 | Toft et al. |
| 5,423,758 A | 6/1995 | Shaw |
| 5,578,011 A | 11/1996 | Shaw |
| 5,755,696 A | 5/1998 | Caizza |
| 5,769,822 A | 6/1998 | McGary et al. |
| 5,843,034 A | * 12/1998 | Redfern et al. ............ 604/110 |
| 5,891,093 A | 4/1999 | Dysarz |
| 5,921,960 A | * 7/1999 | McGary et al. ............ 604/110 |
| 5,935,104 A | * 8/1999 | Janek et al. ............... 604/110 |
| 5,935,113 A | 8/1999 | Dysarz |
| 5,997,507 A | 12/1999 | Dysarz |
| 6,010,486 A | 1/2000 | Carter et al. |
| 6,033,386 A | 3/2000 | Novacek et al. |
| 6,036,674 A | * 3/2000 | Caizza et al. ............ 604/110 |
| 6,050,974 A | 4/2000 | Allard |
| 6,050,977 A | 4/2000 | Adams |
| 6,056,724 A | 5/2000 | Lacroix |
| 6,066,115 A | 5/2000 | Chang Lai |
| 6,099,500 A | 8/2000 | Dysarz |

* cited by examiner

Primary Examiner—Michael J. Hayes
(74) Attorney, Agent, or Firm—Streets & Steele; Jeffrey L. Streets

(57) ABSTRACT

A retractable safety syringe that retracts the needle cannula into the plunger module and destroys the syringe to prevent reuse or an accidental needle prick by destroying the plunger barrier and the cannula barrier within the syringe. The needle cannula is released into the plunger module by shearing the cannula barrier and plunger barrier with an internal annular shear and cutter head. The needle cannula module may be replaced with a layer or smaller needle cannula module thereby allowing a greater selection of needle cannulas.

25 Claims, 13 Drawing Sheets

SELF DESTRUCTIVE SAFETY SYRINGE

BACKGROUND OF THE INVENTION

1. Field of the Invention

This invention relates to a single use syringe for injecting medicine into a patient. More particularly, the invention relates to a safety syringe having a retractable needle cannula that renders the needle cannula harmless after it is used.

2. Background of the Related Art

Many communicable diseases can be spread through the penetration or another having a disease previously used scratching of the skin by a needle that. Spreading of the disease in this manner may occur by accident, such as with medical personnel making injections, or it may occur through misuse, such as by intravenous drug users using a previously used needle cannula.

Various syringes have been invented, designed and developed to retract the needle into the syringe or the plunger inside of the syringe. Some of these devices are U.S. Pat. No. 4,973,316 (Dysarz), U.S. Pat. No. 4,978,343 (Dysarz), U.S. Pat. No. 5,180,369 (Dysarz), U.S. Pat. No. 5,267,961 (Shaw), U.S. Pat. No. 5,019,044 (Tsao), U.S. Pat. No. 5,084,018 (Tsao), U.S. Pat. No. 5,385,551 (Shaw), U.S. Pat. No. 5,389,076 (Shaw), U.S. Pat. No. 5,201,710 (Caselli), and U.S. Pat. No. 6,010,468 (Carter et al). These designs have needles that retract at the end of the injection. Most of these designs have not reached the market due, at least in part, to problems associated with expense of manufacturing, poor reliability or user acceptability. However, even though some of these designs operate poorly and are costly, they have still been commercialised due to the great need in hospitals or clinics for any type of safety syringe.

Most of the existing safety syringe designs allow for automatic retraction of the needle cannula into the plunger barrel of the syringe when the plunger is fully extended into the syringe. The automatic retraction is triggered when the plunger makes physical contact with the distal end of the syringe barrel. Typically, the end of the plunger is provided with a disengageable or sacrificial member at the distal end and the needle cannula is secured by a disengageable or sacrificial member. When the plunger reaches the fully extended position, the physical contact between the plunger and the needle cannula causes activation of the two respective disengageable or sacrificial members. In this manner, the end of the plunger barrel is opened and presented to receive the needle cannula. The needle cannula, no longer secured in position, is biased into the plunger barrel by a spring.

Conventional syringes are typically available in modular systems or kits in which approximately ten different sizes of syringes and approximately ten different sizes of needle cannulas can be used interchangeably. This allows an inventory of twenty items to be used in approximately 100 different combinations in accordance with the present need. However, the safety syringes presently available and described in the above patents are not modular and require stocking of an integral safety syringes for each combination of syringe size and needle cannula size desired, for example 100 different safety syringes. Particularly, in light of the greater cost these syringes, the cost, distribution and storage of safety syringes is much greater than conventional syringes.

Despite the prevalence of modular convention syringes, the emergence of a multitude of safety syringe designs and the increasing public outcry for safety syringes, the complexities of the safety syringe mechanisms have limited the number of attempts to design a safety syringe that is modular. Two such attempts include modular syringe tip designs that are combined with a conventional syringe as described in U.S. Pat. No. 5,891,093 (Dysarz), U.S. Pat. No. 5,935,113 (Dysarz). Compared with the foregoing automatically retracting safety syringes, these two designs can be considered to have safety needle cannula assemblies that are self-contained and manually operated, while being connectable to a conventional syringe and with a conventional locking arrangement. While these devices serve the aforementioned need for modularity, the obvious drawbacks to the devices include the manual retraction mechanism and the additional length that the needle cannula assembly adds to the syringe.

Another design utilises a modified luer-lok that requires pressed fittings, a cutting ring, and a frangible portion that are to be activated or actuated at the same time requiring more hand and finger strength of the user which many medical people do not have. Still another problem with this design is that the needle cannula must be pushed and moved in the direction of the distal end of the needle cannula and if the needle cannula is in an artery or a vein at the time, the needle cannula will pierce the other side of the artery or vein and deposit medication into an undesirable area of the body. Still yet another problem with this design, the plunger tip must enter a restricted area of the luer-lok and restrict and trap the medication still contained in the area of the stopper. And still yet another problem with this design is that when the outer hub is being attached to the luer-lok, the proximal end of the inner hub could be hit by the distal end of the luer-lok fitting and cause the frangible portion to break or otherwise fail.

Each of the foregoing designs has various disadvantages. There are parts that work in a difficult and complicated manner and could be expensive to manufacture. These designs could also be difficult to operate.

The need exists for a safe and disposable syringe that also cannot be reused and still use standard needle cannula of any verity.

SUMMARY OF THE INVENTION

It is the object of the present invention to provide a safety syringe module with a safety needle cannula module wherein the safety syringe module reacts with the safety needle cannula module in such a manner that will cause the needle cannula to retreat into the safety syringe module.

Another object of the present invention is to render the needle cannula useless after the needle cannula is retracted into the syringe module to prevent the accidental reuse of a contaminated needle cannula or to further prevent the reuse by users of illicit drugs.

It is still yet another object of the present invention to allow a hospital or clinic etc., to keep a lesser inventory of safety syringes and safety needle cannulas.

The present invention, in at least certain embodiments, provides a syringe with a syringe body with a syringe channel there through, needle cannula apparatus connected to the syringe body with a cannula body and a cannula channel there through, a needle with a needle channel there through and a needle flange at one end, a plunger movably disposed in the syringe channel for pushing fluid in the syringe channel and out through the needle channel, the plunger having a plunger channel there through, a cannula barrier, the needle flange abutting the cannula barrier, the cannula barrier initially preventing the needle cannula from moving into the syringe body, the cannula barrier having a cannula barrier channel there through, a cutter head on the plunger, and a cutter head channel there through, a plunger barrier adjacent the cutter head and initially closing off the plunger interior to fluid, the plunger barrier movable with the cutter head within the syringe body, and the cutter head movable by moving the plunger to break the plunger barrier and the cannula barrier to free the needle cannula so the needle cannula is movable through the cutter head and into the plunger channel. In certain aspects, an optional spring apparatus in the cannula channel urges the needle cannula into the plunger channel upon breaking of the cannula barrier and the plunger barrier.

DETAILED DESCRIPTION OF THE PREFERRED EMBODIMENTS

Figure 1:
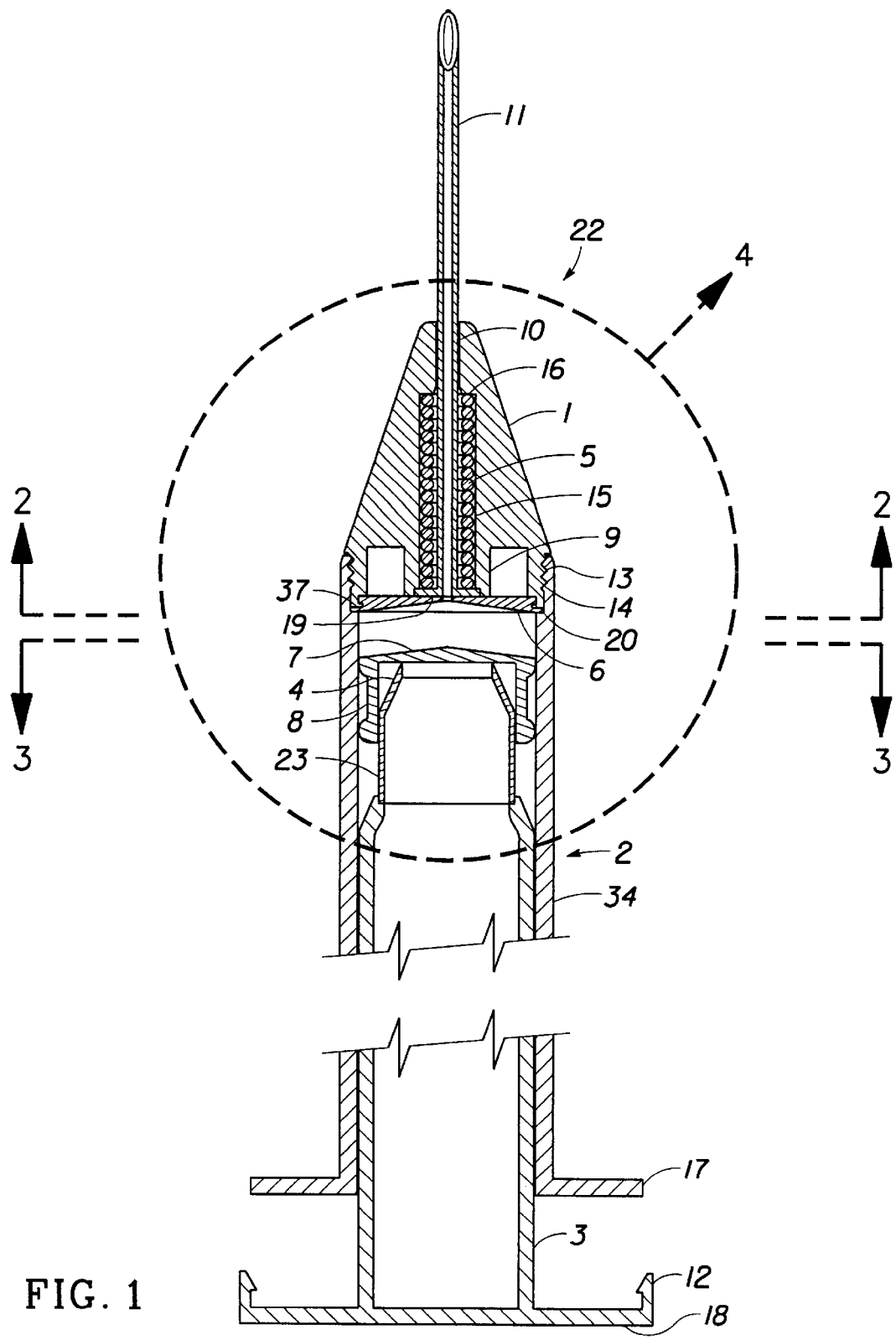
FIG. 1 is a section elevation view of the safety needle cannula module and safety syringe plunger module.

Referring To FIG. 1 there is shown a section elevation of the syringe 2 with the needle cannula module 1 that is fixed to a syringe body 34.

The syringe body 34 is an elongated hollow tube with an inside surface and an outside surface. The distal end of the syringe body has syringe module threads 13 formed on the outside surface. The proximal end of the syringe body has a finger flat 17.

The needle cannula module 1 is comprised of a needle cannula 11 with the distal end having a point and a proximal end fixed to a needle cannula flange 19. A cannula tunnel 10 is formed in the needle cannula module that extends from the distal end to the proximal end. The proximal end of the needle cannula 11 is further disposed in a biased spring 5. The distal end of the biased spring is abutting and thrusting or urged against the cannula flat 16 and the proximal end of the biased spring is thrusting against the distal end of the needle cannula flange. The needle cannula is also shown disposed in the cannula tunnel 10. The biased spring 5 is also shown disposed in the annular spring guide 15.

The barrier cannula 6 is shown with an annular recess and is suitably fixed to the proximal end of the needle cannula module 1 forming a fluid tight and gas tight seal between the proximal end of the needle cannula module and near the distal end of the syringe body 34. The outer periphery of the barrier cannula also forms the needle cannula module gasket 20 or seal. The needle cannula module gasket project outwardly into the recess 37 formed between the syringe body and the needle cannula module. The barrier cannula 6 is made out of a shearable or cuttable material.

The plunger module 3 is shown disposed in the elongated hollow barrel of the syringe body 34. The proximal end of the plunger module 3 is shown with a thumb flat 18 and a plunger lock 12 on the outer periphery of the thumb flat. The thumb lock 12 locks onto the finger flat 17. The plunger module has an elongated tunnel that extends from the distal end to the proximal end or the plunger module.

The distal end of the plunger module is suitably fixed to the annular shear foundation 23. The distal end of the annular shear foundation is fixed to the proximal end of the annular shear and cutter head 4. The distal end of the annular shear and cutter head 4 is formed into a cutting edge for cutting and shearing the plunger barrier 7 and the barrier cannula 6. The annular cone shear and cutter head 4 is supporting the plunger barrier 7 that is made out of a shearable material. The plunger barrier 7 is shown partially supported by the annular cone shear and cutter head and the plunger gasket 8. The plunger gasket 8 is supported on the outer surface of the annular shear foundation. The plunger module and the plunger gasket thrust fluid through the syringe body and into the needle cannula for expulsion from needle cannula.

The needle cannula module 1 is fixed to the syringe body 34 by the module threads 13 and the cannula module threads 14. This could also be a slip on or friction connection or it could be a snap on connection by design choice.

Figure 2:
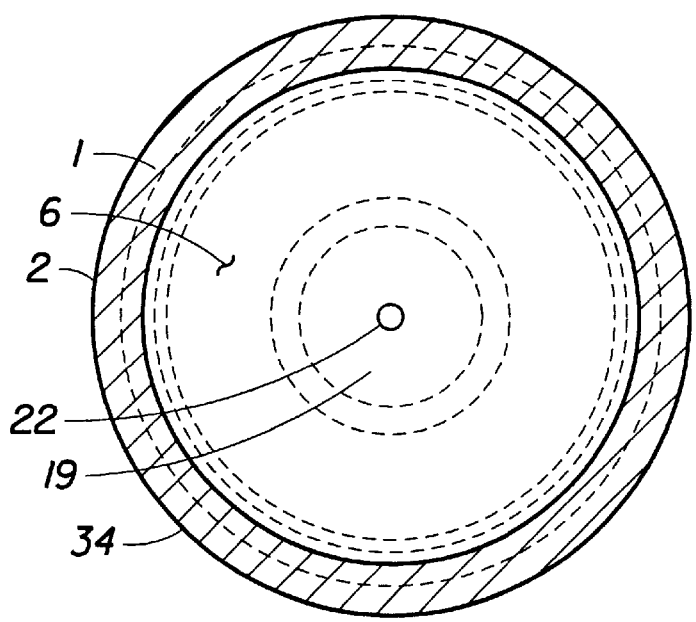
FIG. 2 is a section plan view as taken through FIG. 1

Referring to FIG. 2 there is shown a section plan view of the barrier cannula 6 as taken through FIG. 1. The cannula 22 is shown essentially near the center of the barrier cannula. The needle cannula flange 19 is shown behind the barrier cannula. The outer periphery of the barrier cannula is the needle cannula module 1 and the syringe body 34.

Figure 3:
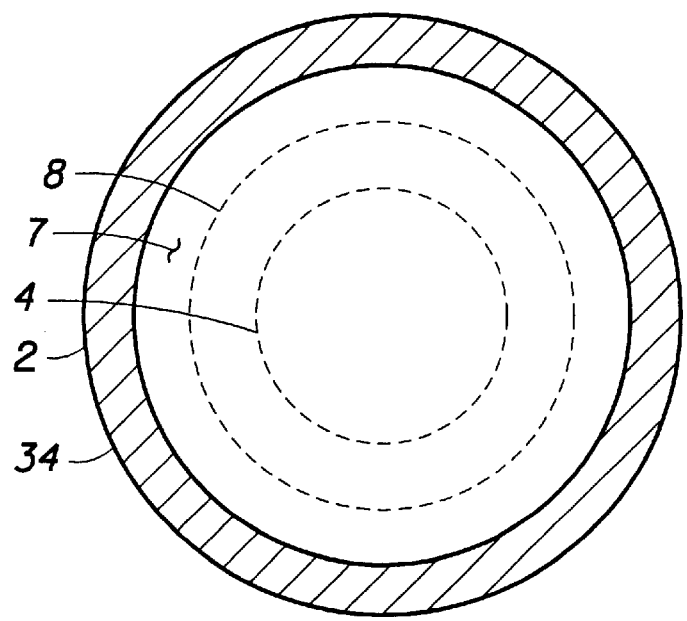
FIG. 3 is a section plan view that is taken through FIG. 1

Referring To FIG. 3 there is shown a section plan view of the plunger barrier 7 as taken through FIG. 1. The syringe body 34 is shown at the outer periphery, the plunger gasket 8 and the annular cone shear and cutter head 4 are shown toward the center of the plunger barrier.

Figure 4:
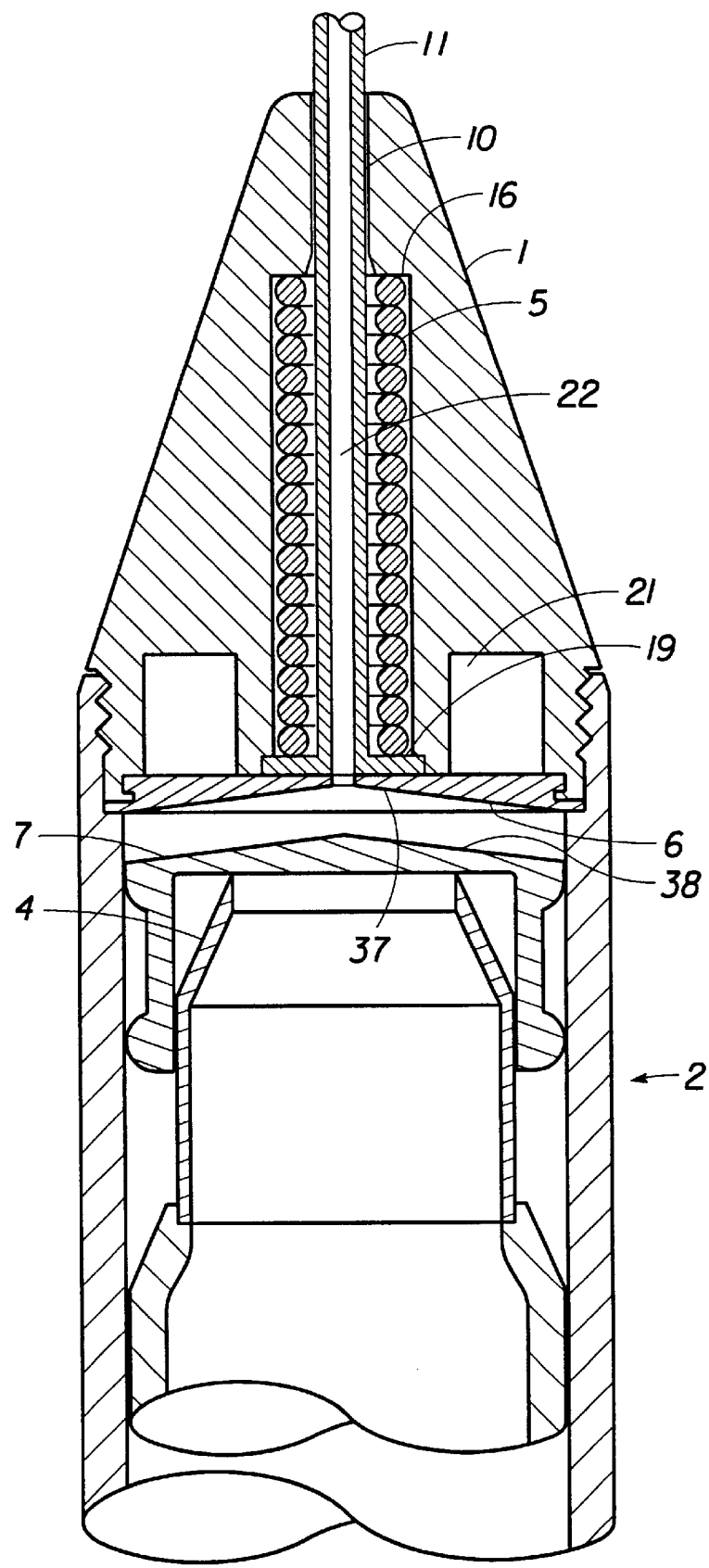
FIG. 4 is an enlarged section elevation of the distal end of the safety needle cannula module and the safety syringe and plunger module.

Referring to FIG. 4 there is shown an enlarged section elevation of the distal end of the syringe 2 and the entire needle cannula module 1

The needle cannula 11 is extending from the cannula tunnel 10 and the proximal end of the biased spring 5 is abutting, thrusting and urging on the distal end of the needle cannula flange 19. The distal end of the biased spring is abutting, thrusting and urging on the cannula flat 16. The barrier cannula 6 is sufficiently rigid to retain the biased spring. The barrier cannula 6 is also shown with a barrier recess 37 formed in the proximal end of the barrier cannula. The plunger barrier 7 has a plunger projection 38 wherein the plunger projection conforms with the barrier recess so that medication fluid is not wasted when the barrier recess comes in contact with the plunger projection and the cannula 22 is also closed off to stop fluid flow to the needle cannula. The annular shear and cutter head depository 21 is shown formed in the proximal end of the needle cannula module 1 to allow the annular shear and cutter head 4 sufficient space to complete the shearing or cutting process.

The plunger barrier 7 is shown at the distal end of the annular shear and cutter head 4.

Figure 5:
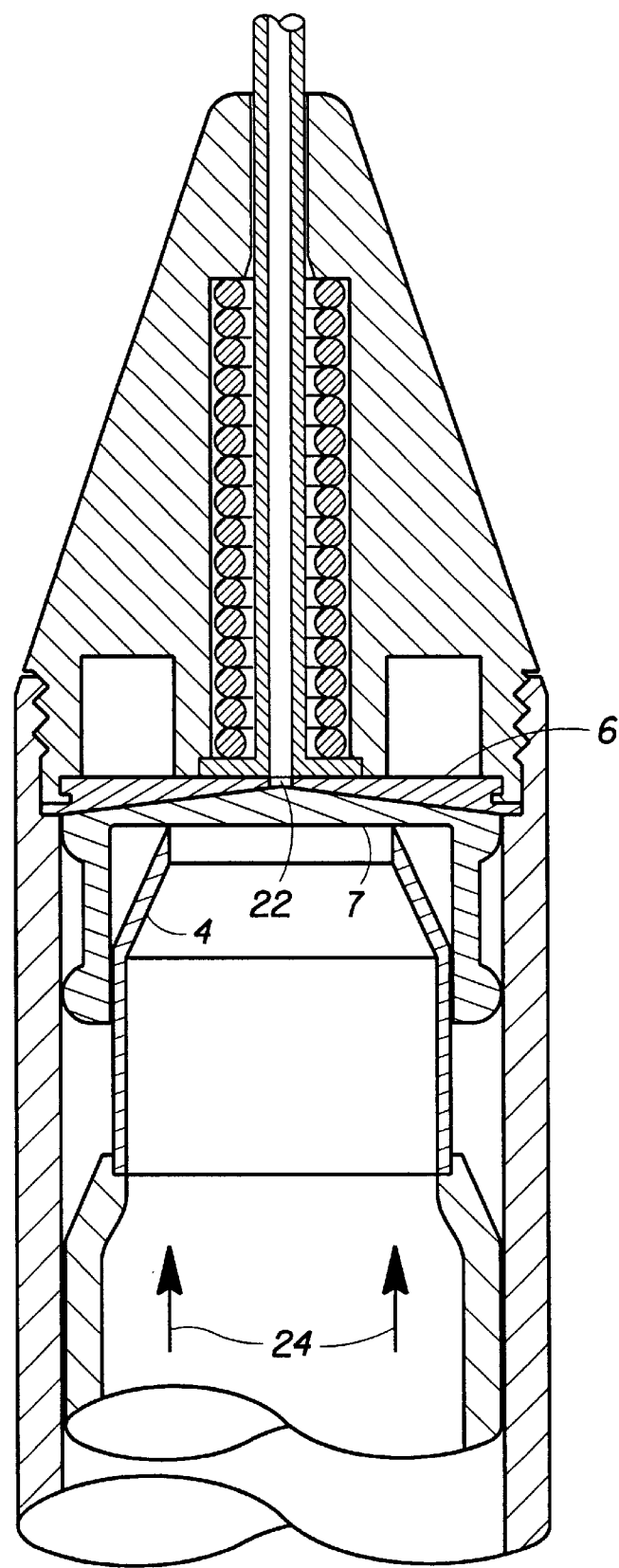
FIG. 5 is an enlarged section elevation showing the plunger module moving towards the safety needle cannula module.

Referring to FIG. 5 there is shown a section elevation of the annular cone shear and cutter head 4 moving in a distal direction 24. The plunger barrier 7 is shown pushed into the barrier cannula 6 thereby blocking the cannula 22 after all medication has been injected into a body.

Figure 6:
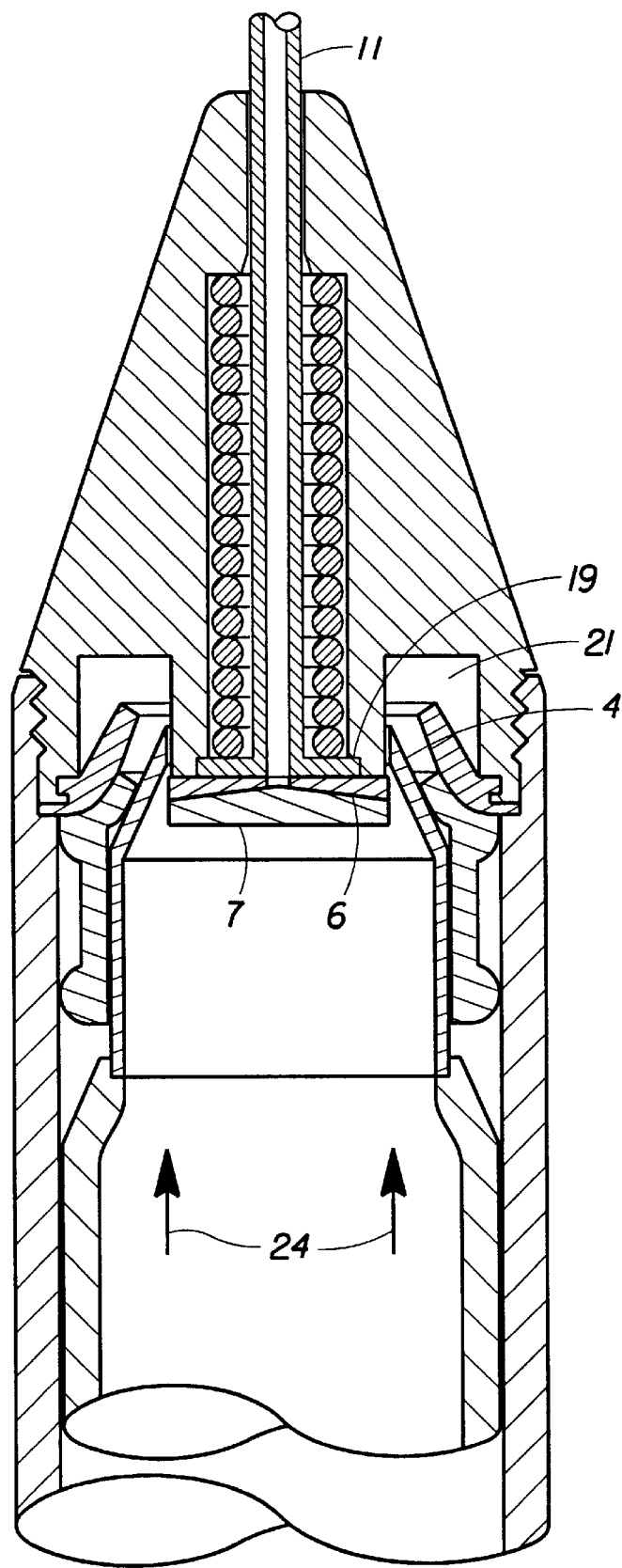
FIG. 6 is an enlarged section elevation of the plunger module interacting with the safety needle cannula module.

Referring to FIG. 6 There is shown a section elevation view of the annular cone shear and cutter head 4 moving in a distal direction 24 after having sheared or cut a tunnel in the plunger barrier 7 and the barrier cannula 6 thereby releasing the needle cannula 11 and the biased spring 5. It should be noted that FIG. 6 will be as shown for just a brief moment.

The annular shear and cutter head is shown in the annular shear and cutter head depository 21.

Figure 7:
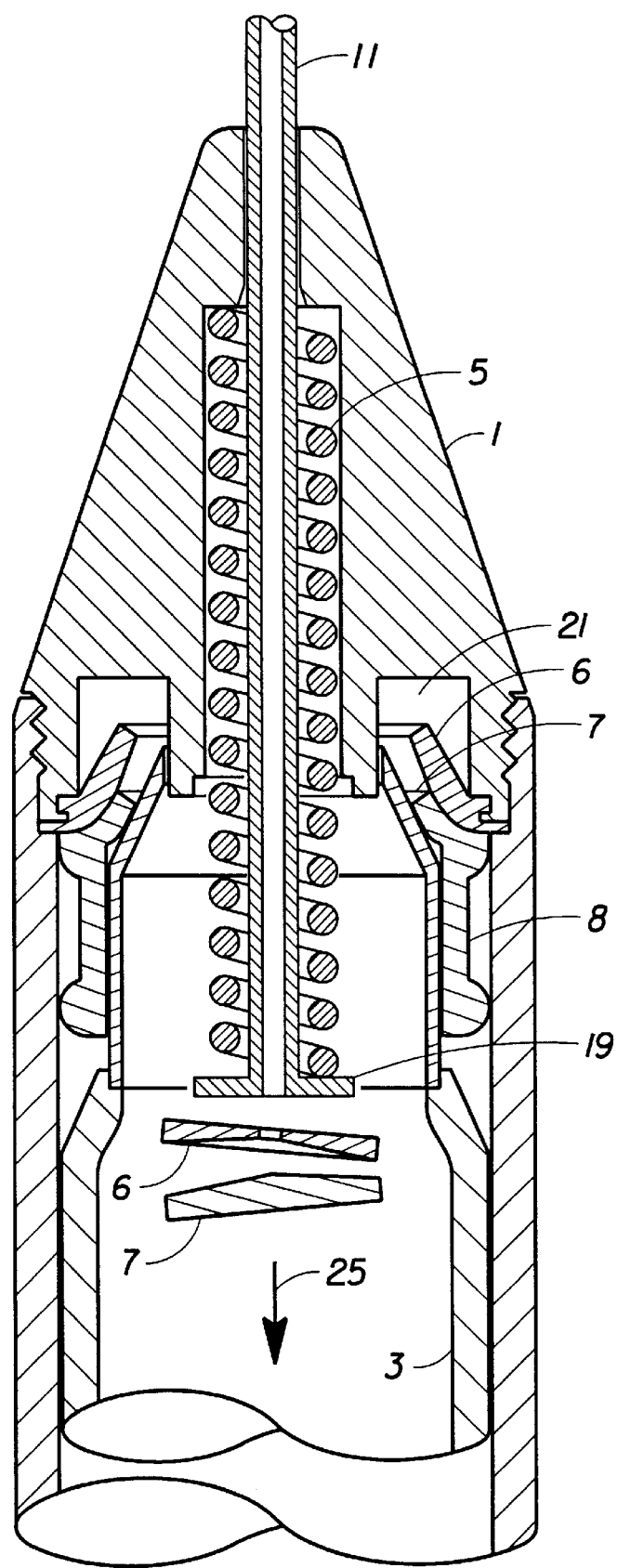
FIG. 7 is an enlarged section elevation of the biased spring thrusting the needle cannula into the plunger module.

Referring To FIG. 7 there is shown a section elevation view of the biased spring 5 thrusting or urging on the distal end of the needle cannula flange 19 and thrusting the needle cannula 11 into the tunnel inside of the plunger module 3.

Part of the barrier cannula 6 and part of the plunger barrier 7 are shown being thrust into or falling to the inside of the plunger module 3 in a proximal direction 25. The remainder of the barrier cannula 6 and the plunger barrier 7 are shown bent or curved in or near annular shear and cutter head depository 21. The plunger gasket 8 has been moved in a proximal direction 25 relative to the annular shear foundation 23 that is part of the distal end of the plunger module 3.

Figure 8:
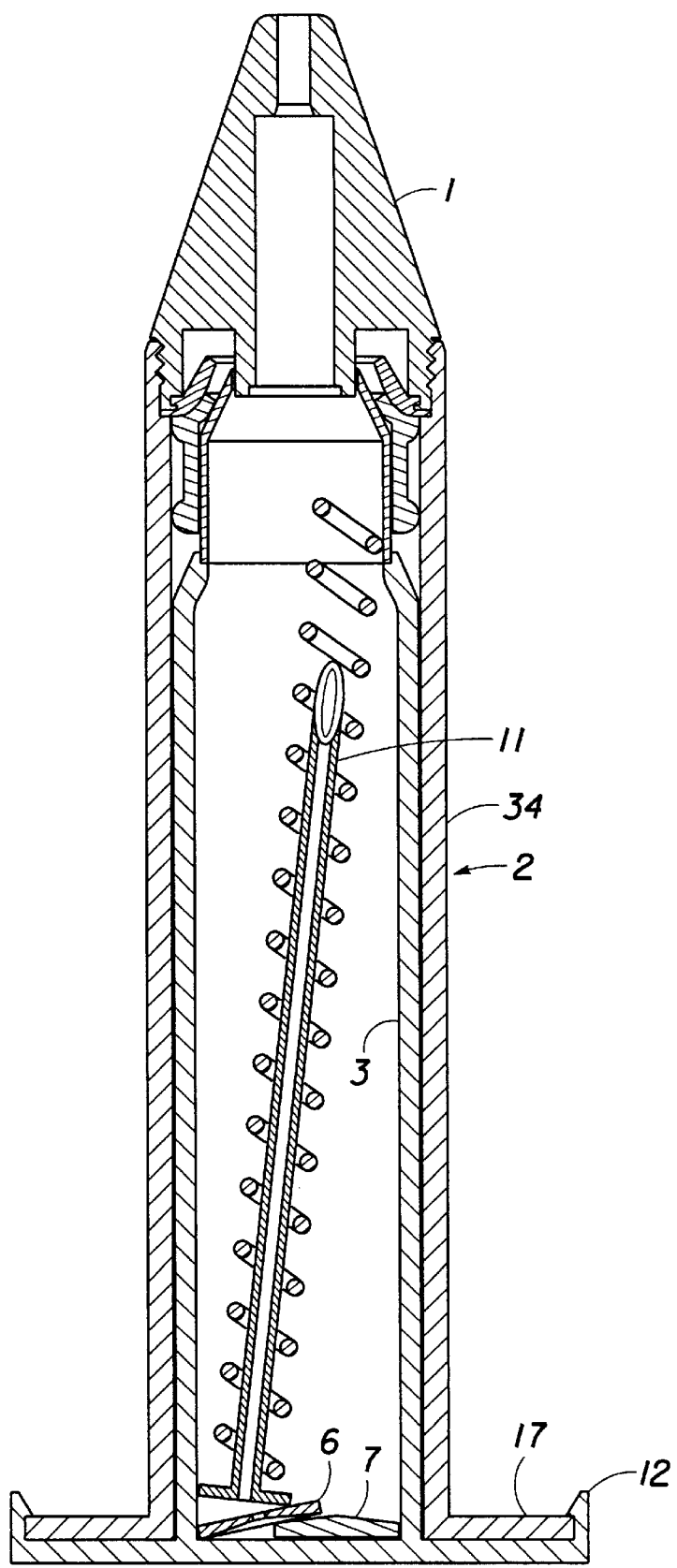
FIG. 8 is a section elevation of the needle cannula contained in the plunger module.

Referring to FIG. 8 there is shown a section elevation of the needle cannula module 1 fixed to the syringe body 34 and plunger module 3 with the needle cannula 11 secure inside of the plunger module tunnel. Part of the barrier cannula 6 and the plunger barrier 7 are contained in the plunger module tunnel.

The plunger lock 12 is shown latched onto the finger flat 17 thereby locking the plunge module to the syringe body 34 to prevent the plunger from being accidentally pulled out and exposing the needle cannula.

Figure 9:
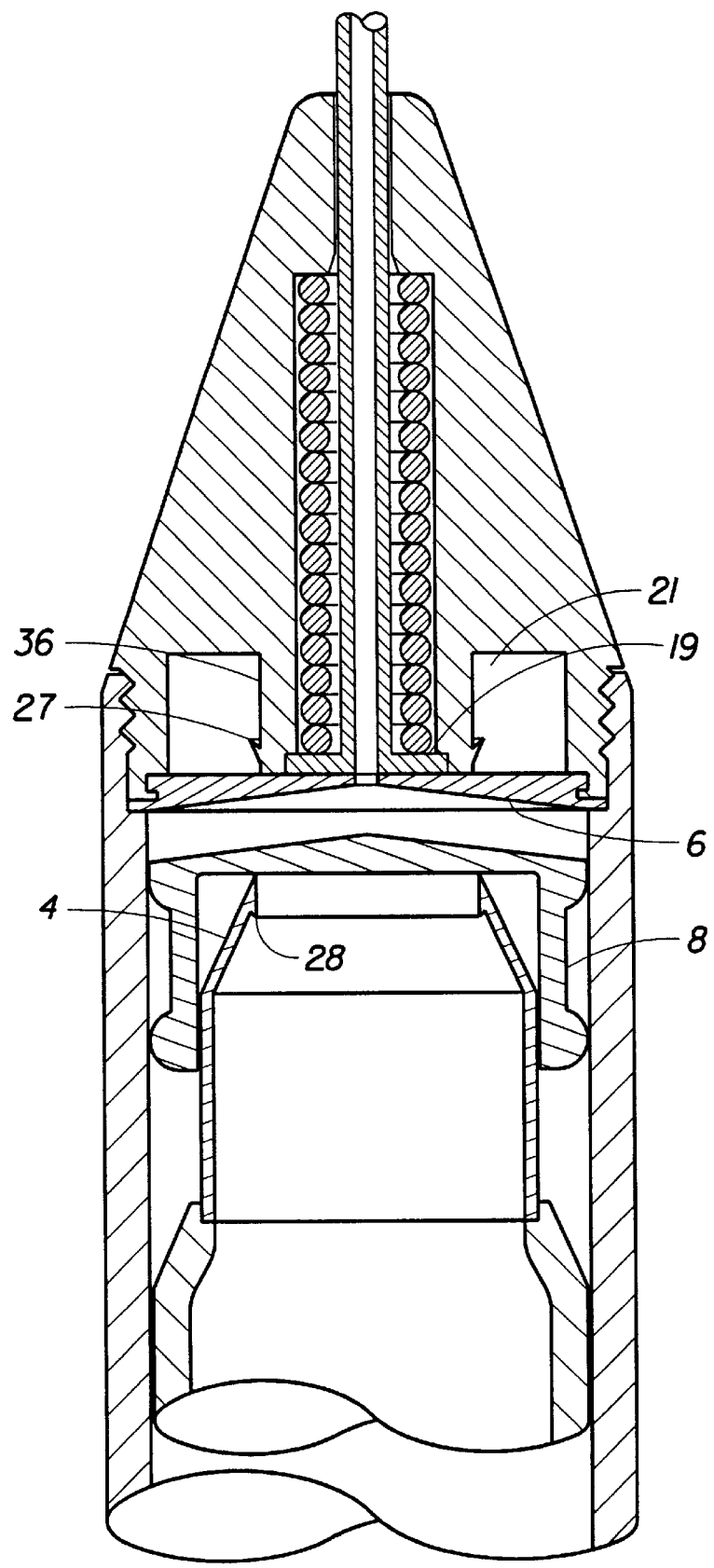
FIG. 9 is a section elevation of the plunger module and the needle cannula module with a latch and retainer means.

Referring to FIG. 9 there is shown an enlarged section elevation of the device of the preferred embodiment with an internal locking means.

The internal locking means is comprised of a circumferential latch 27 that is formed on the outside perimeter of the cannular hub 36. The slipover retainer member 28 is shown formed on the inside surface of the annular shear and cutter head 4. The slip over retainer member 28 is positioned for engaging the circumferential latch 27 on the cannular hub 36.

Figure 10:
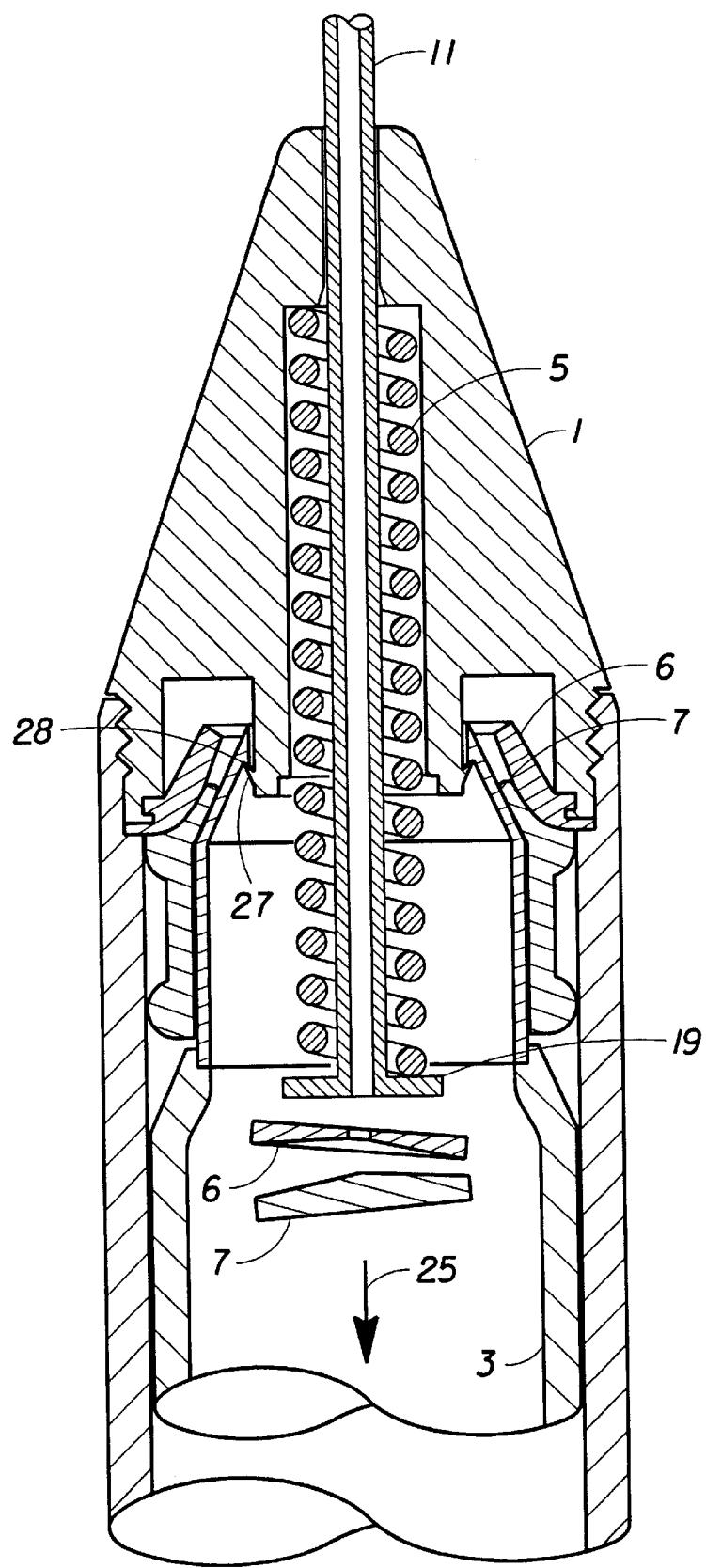
FIG. 10 is a section elevation showing the latch and the retainer engaged.

Referring to FIG. 10 there is shown a section elevation of the internal locking means engaged. The needle cannula 11 is being thrust into the plunger module 3 by the biased spring 5 thrusting on the needle cannula flange 19, part of the plunger barrier 7, and part of the barrier cannula 6 inside of the plunger module 3.

The proximal end of the slip over retainer 28 has been pushed past the distal end of the circumferential latch 27 and thus snapped over the circumferential latch 27 thus locking the slip over retainer to the circumferential latch thereby engaging and locking the plunger module 3 to the needle cannula module 1.

By providing a locking fitting, an internally destroyed syringe and the completely encapsulated needle cannula the entire syringe is destroyed and cannot be reused again. The plunger gasket 8 is shown having been moved in a proximal direction 25 relative to the distal end of the plunger module 3.

Figure 11:
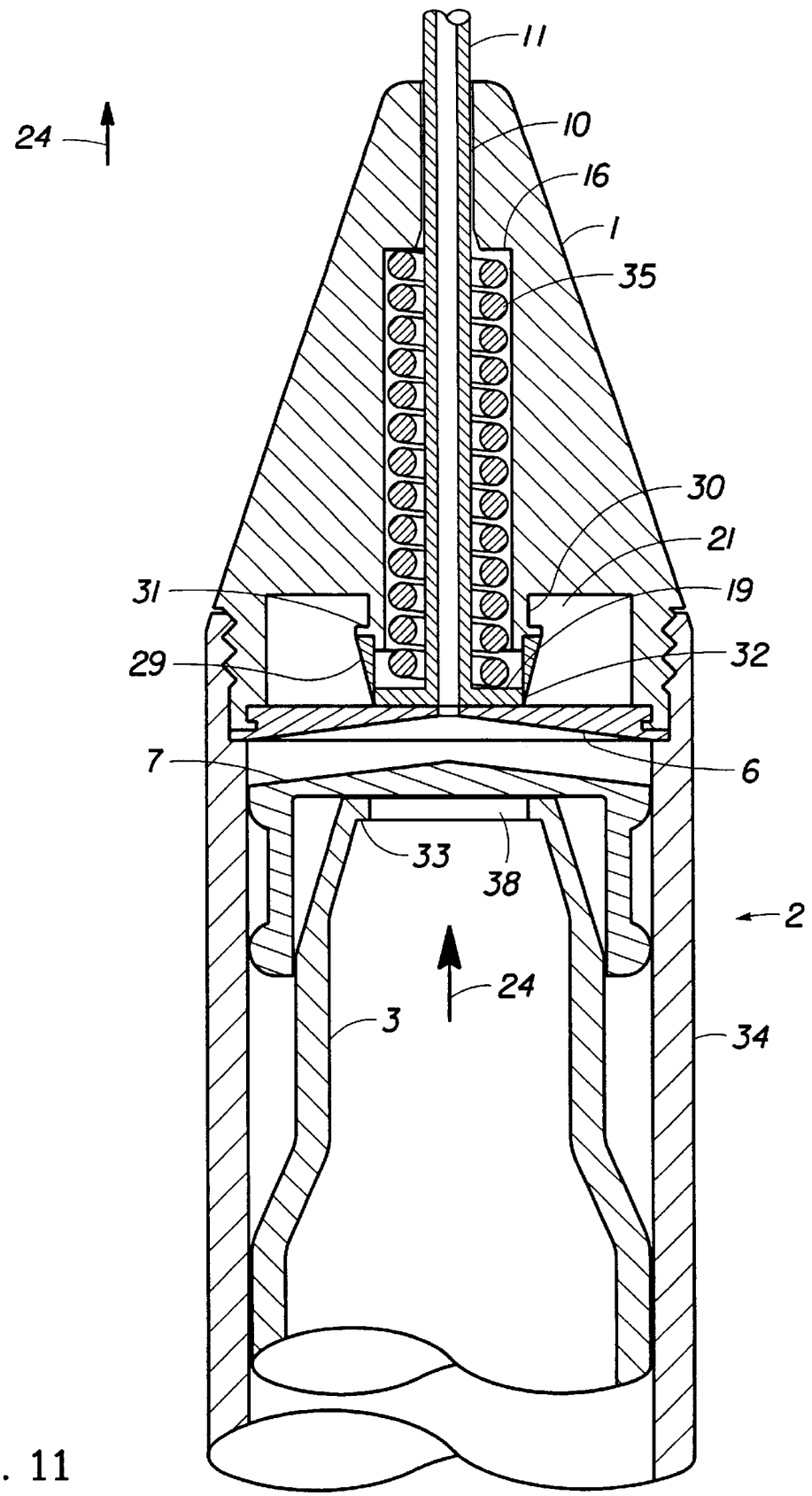
FIG. 11 is a section elevation with an inverted cutter head.

Referring to FIG. 11 there is shown a section elevation view of the syringe 2 with the needle cannula module 1 suitably fixed to the syringe body 34 with a plunger module 3 inside of the syringe body 34. All of the components such as the needle cannula 11, the cannula tunnel 10, the cannula flat 16, the annular cutter head depository 21, are all similar to FIG. 1.

The inverted cutter head 29 is shown disposed about the annular cutter head foundation 30 and the cutter head flange 31. The inverted cutter head is shown supported on the proximal end of the annular cutter head foundation 30. The cutter head flange 31 is shown formed on the outer periphery of the annular cutter head foundation. The invented cutter head is shown with the sharp edge 32 directed toward the barrier cannula 6.

The partial biased spring 35 is shown thrusting or urging the needle cannula flange 19 and the needle cannula 11 into the barrier cannula 6, however the partial biased spring 35 is shown as partially compressed with gaps between the coils to allow the partial biased spring to be further compressed thereby allowing the needle cannula flange 19 to be moved in a distal direction 24, thereby exposing the sharp edge 32 of the inverted cutter head 29 to the barrier cannula and the plunger barrier 7 on the distal end of the plunger module 3. The partial biased spring does not have sufficient thrust or force to push or urge the needle cannula flange past the barrier cannula 6.

The distal end of the plunger module 3 is shown moving in a distal direction 24. The plunger barrier support flange 33 is shown supporting the plunger barrier as the plunger module is urged in a distal direction 24. A needle cannula passage 38 is shown formed in the distal end of he plunger module 3.

Figure 12:
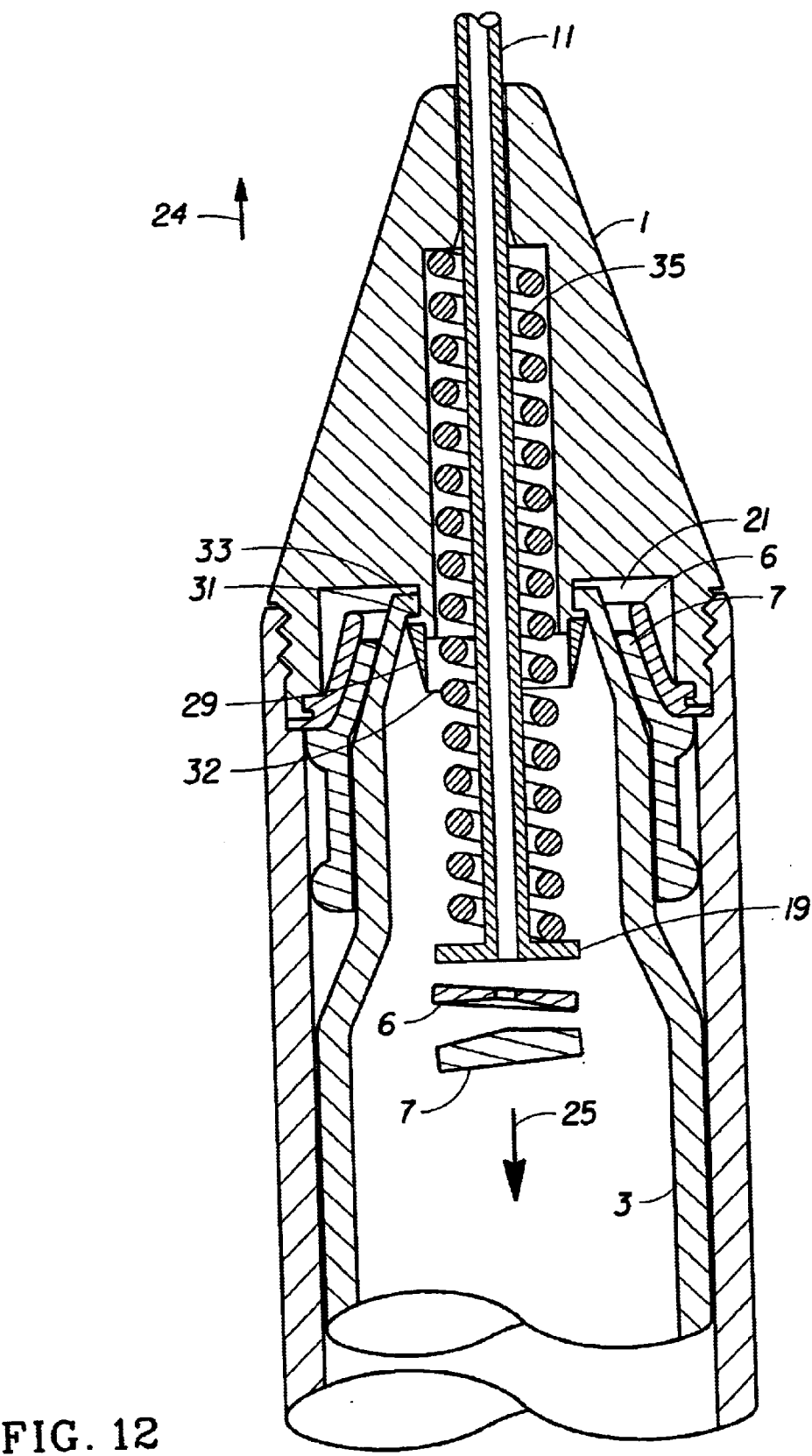
FIG. 12 is a section elevation describing how the inverted cutter head operates.

Referring to FIG. 12 there is shown a section elevation of the second device of the preferred embodiment being internally destroyed. The plunger barrier support flange 33 has thrust the plunger barrier 7 and the barrier cannula 6 into the inverted cutter head 29 and the needle cannula flange 19. The needle cannula flange 19 has moved in a distal direction 24 further compressing the partial biased spring 35 thereby exposing the barrier cannula 6 and the plunger barrier 7 to the sharp edge 32 of the inverted cutter head 29 and urging the barrier cannula and plunger barrier onto the sharp edge of the inverted cutter head wherein the inverted cutter head 29 has cut a passage or tunnel through the barrier cannula and the plunger barrier thus allowing the partial biased spring 35 to thrust the needle cannula flange 19 and the needle cannula 11 in a proximal direction 25 into the inside of the plunger 3 where the needle cannula 11 will be completely covered to prevent an accidental needle stick.

The plunger barrier support flange 33 has been thrust past the inverted cutter head and has been further locked onto the distal end of the cutter head flange 31 wherein the inverted cutter head has been moved through the cannula passage where it will be captured in the distal end or tunnel of the plunger module 31.

Figure 13:
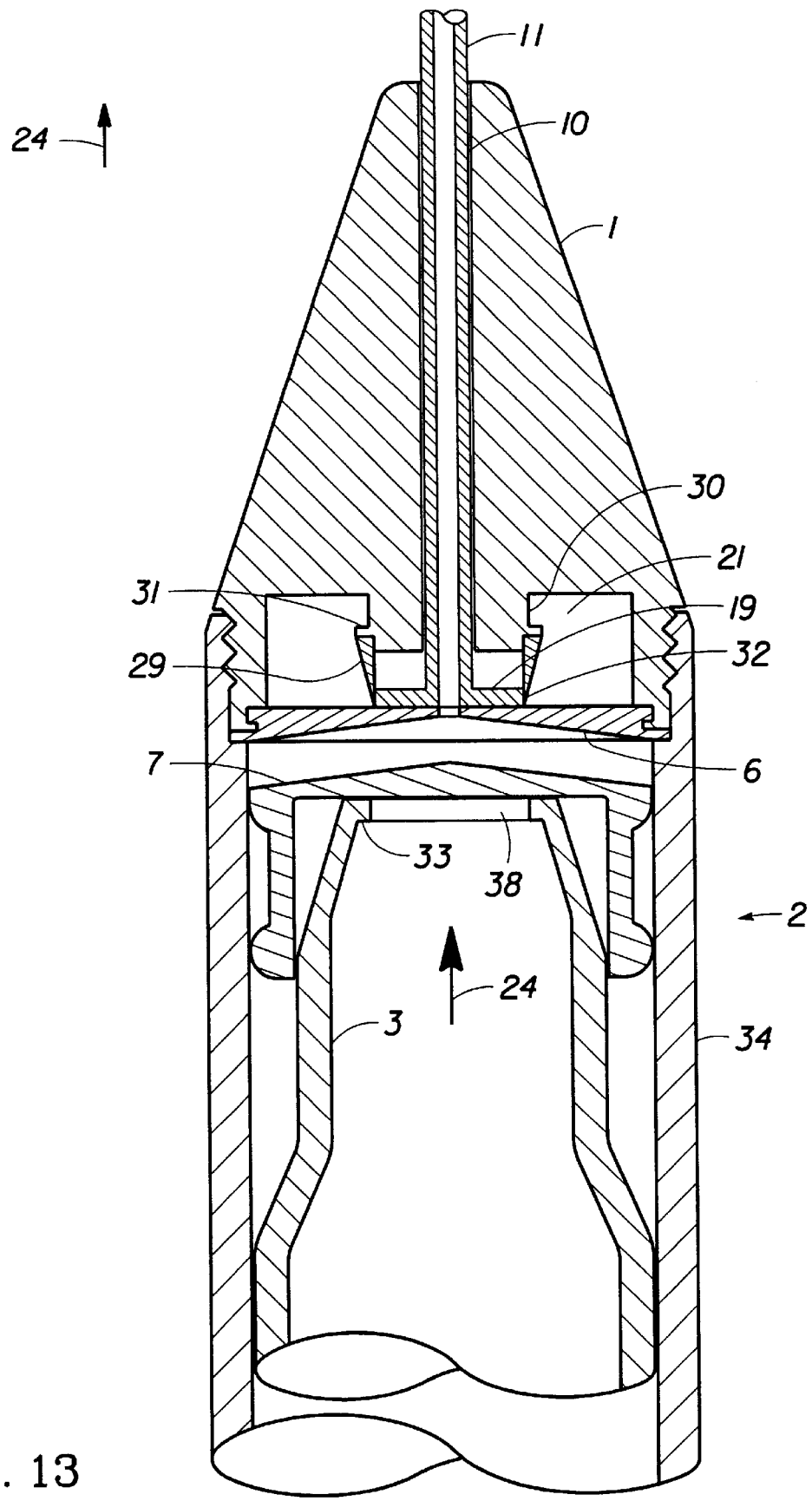
FIG. 13 is a section elevation of a springless syringe.

Referring to FIG. 13 there is shown a section elevation view of the syringe 2 with the needle cannula module 1 suitably fixed to the syringe body 34 with a plunger module 3 inside of the syringe. Most of the components such as the needle cannula 11, the cannula tunnel 10, and the plunger module 3 the plunger barrier 7 and the annular shear and cutter head depository 21 are similar to FIG. 11.

The inverted cutter head 29 is shown disposed about the annular cutter head foundation 30 and the cutter head flange 31. The inverted cutter head is shown supported on the proximal end of the annular cutter head foundation 30. The cutter head flange 31 is shown formed on the outer periphery of the annular cutter head foundation. The inverted cutter head is shown with the sharp edge 32 directed toward the barrier cannula 6. The barrier cannula 6 is holding the needle cannula 11 and the needle cannula flange 19 in place with adhesive or the barrier cannula and the needle cannula flange could be one piece.

The distal end of the plunger 3 is shown moving in a distal direction 24. The plunger barrier support flange 33 is shown supporting the plunger barrier as the plunger module is urged in a distal direction 24. A needle cannula passage 38 is shown formed in the distal end of the plunger 3.

Figure 14:
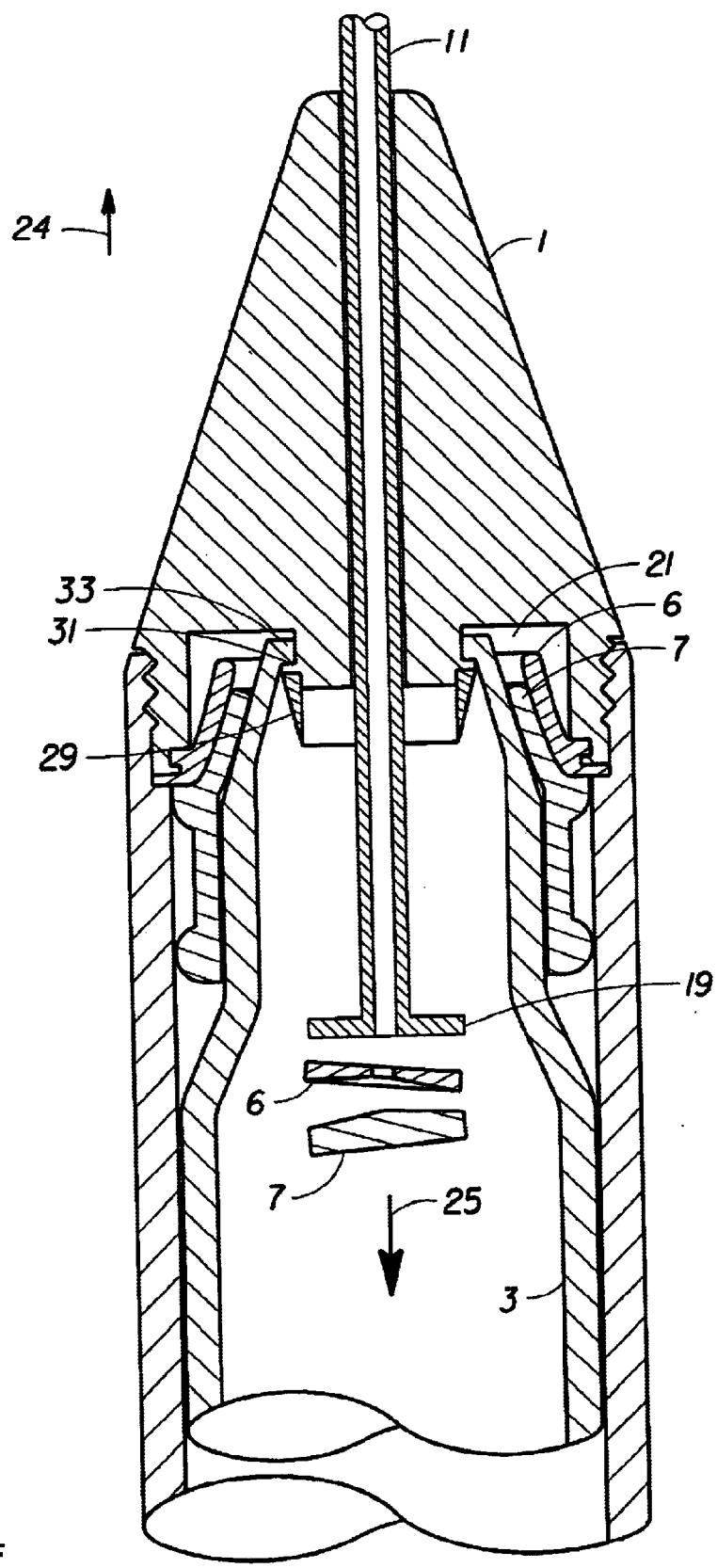
FIG. 14 is a section elevation of the springless syringe being destroyed.

Referring to FIG. 14 there is shown a section elevation of the second device of the preferred embodiment being internally destroyed. The plunger barrier support flange 33 has thrust the plunger barrier 7 and the barrier cannula 6 into the inverted cutter head 29 and the needle cannula flange 19. The needle cannula flange 19 has moved in a distal direction 24 thereby exposing the barrier cannula 6 and the plunger barrier 7 to the sharp edge 32 of the inverted cutter head 29. As the plunger module further moves in a distal direction the plunger barrier support flange 33 urges or thrusts the barrier cannula and the plunger barrier onto the sharp edge of the inverted cutter head wherein the inverted cutter head 29 cuts or shears a passage through the barrier cannula and the plunger barrier thus allowing the needle cannula 11 to fall in a proximal direction 25 into the inside of the plunger 3 where the needle cannula 11 will be completely covered to prevent an accidental needle stick.

The plunger barrier support flange 33 has been thrust past the inverted cutter head and has been further locked onto the distal end of the cutter head flange wherein the inverted cutter head has been moved through the cannula passage 38 where it will be captured in the distal end of the plunger module 3.

The present invention, therefore, provides in certain, but not necessarily all embodiments, a syringe with a syringe body with a first body end and a second body end and a syringe channel there through from the first body end to the from the first body end to the second body end, needle cannula apparatus connected to the syringe body and with a cannula body having a first cannula end and a second cannula end, and a cannula channel extending from the first cannula end to the second cannula end, a needle having a first needle end and a second needle end, the first needle end projecting from and extending beyond the cannula body, the second needle end within the cannula channel, the needle having a needle channel there through from the first needle end to the second needle end, the needle having a needle flange at the second needle end, a plunger with a first plunger end and a second plunger end, the first plunger end movably disposed in he syringe channel for pushing fluid in the syringe channel to and through the needle channel for expulsion out from the first needle end, the plunger having a plunger channel from the first plunger end to the second plunger end, a cannula barrier connected to the cannula body and extending across the second cannula end, the needle flange abutting he cannula barrier, the cannula barrier initially preventing the needle cannula from moving into the syringe body, the cannula barrier having a cannula barrier channel there through permitting fluid communication between the syringe channel and the needle channel, a cutter head at the first plunger end and having a first cutter end, a second cutter end, and a cutter head channel there through from the first cutter end to the second cutter end, a plunger barrier adjacent the cutter head and initially closing off the first cutter head movable by moving the plunger to break the plunger barrier and the cannula barrier to free the needle cannula so the needle cannula is movable through the cutter head and into the plunger channel. Such a method may include one or some (in any possible combination) of the following: spring apparatus in the cannula channel for urging the needle cannula into the plunger channel upon breaking of the cannula barrier and the plunger barrier; the cannula channel having a top edge, and the spring apparatus including a spring with a first spring end abutting and urged against the top edge of the cannula channel and a second spring end abutting and urged against the needle flange; wherein the spring is movable into the plunger channel; the cannula barrier having a recess, the cannula body having a cannula lip projecting inwardly and disposed in the recess; wherein the cannula body has an interior circumferential channel, the cutter head having an upper cutting edge sized and configured for receipt within the interior circumferential channel and for facilitating breaking of the plunger barrier and the cannula barrier by the cutter head; wherein the cannula barrier has a cannula barrier lip seal disposed between a lower edge of the cannula body and an upper shoulder of the syringe body; wherein the cannula barrier has a barrier recess formed in a bottom surface hereof and the plunger barrier has a plunger projecting portion projecting from a top surface thereof, the barrier recess and the plunger projecting portion each having a corresponding shape for mating abutment of the plunger barrier against the cannula barrier so that fluid flow to the needle channel is closed off upon said abutment, the plunger movable to move the plunger barrier into abutment against the cannula barrier; seal apparatus projecting from the plunger barrier for sealing off a space between an interior surface of the syringe body and an exterior surface of the cutter head, thereby preventing fluid in the syringe body from flowing into said space; wherein an upper portion of the seal apparatus is deformable against the cannula barrier when pushed there against; first locking apparatus for locking the cutter head to the cannula body after the cutter head has broken the plunger barrier and the cannula barrier; wherein the first locking apparatus has a cannula hub within the cannula body defined by a projecting hollow cylindrical body encompassing a portion of the needle cannula, a latch member on an exterior surface of the cannula hub, and a retainer member on the cutter head positioned for engaging the latch member of the cannula hub to lock the cutter head and the plunger connected thereto to the cannula hub preventing movement of the plunger; second locking apparatus for locking the plunger to the syringe body; wherein the second locking apparatus has syringe flange at the second body end, and the plunger with a plunger with a plunger retainer member at the plunger second end, the plunger retainer member movable to engage the syringe flange to lock the plunger to the syringe body; wherein the needle cannula apparatus includes a plurality of cannula bodies each with a needle cannula of a different gauge, each cannula body connectable to the syringe body; and/or the first body end of the syringe body having interior threads, the second cannula end of the cannula body having exterior threads for threadily mating with the interior threads of the first body end of the syringe body to connect the cannula apparatus to the syringe body.

The present invention, therefore, provides in certain, but not necessarily all embodiments, a syringe with a syringe body with a first body end and a second body end and a syringe channel there through from the first body end to the second body end, needle cannula apparatus connected to the syringe body and with a cannula body having a first cannula end and a second cannula end, and a cannula channel extending from the first cannula end to the second cannula end, a needle having a first needle end and a second needle end, the first needle end projecting from and extending beyond the cannula body, the second needle end within the cannula channel, the needle having a needle channel there through from the first needle end to the second needle end, the needle having a needle flange at the second needle end, a plunger with a first plunger end and a second plunger end, the first plunger end movably disposed in the syringe channel for pushing fluid in the syringe channel to and through the needle channel for expulsion out from the first needle end, the plunger having a plunger channel from the first plunger end to the second plunger end, a cannula barrier connected to the cannula body and extending across the second cannula end, the needle flange abutting the cannula barrier, the cannula barrier initially preventing the needle cannula from moving into the syringe body, the cannula barrier having a cannula barrier channel there through permitting fluid communication between the syringe channel and the needle channel, a cutter head at the first plunger end and having a first cutter end, a second cutter end, and a cutter head channel there through form the first cutter end to the second cutter end, a plunger barrier adjacent the cutter head and initially closing off the first cutter end, the plunger barrier movable with the cutter head within the syringe body, the cutter head movable by moving the plunger to break the plunger barrier and the cannula barrier to free the needle cannula so the needle cannula is movable through the cutter head and into the plunger channel, first locking apparatus for locking the cutter head to the cannula body after the cutter head has broken the plunger barrier and the cannula barrier, and second locking apparatus for locking the plunger to the syringe body. Such a method may include one or some (in any possible combination) of the following: spring apparatus in the cannula channel for urging the needle cannula into the plunger channel upon breaking of the cannula barrier and the plunger barrier; and/or wherein the needle cannula apparatus includes a plurality of cannula bodies each with a needle cannula of a different gauge, each cannula body connectable to the syringe body.

What is claimed as invention:

1. A syringe, comprising:
   a syringe body with a distal end and a proximal end, wherein the syringe body is an elongated hollow tube with an inside surface and an outside surface;
   a needle cannula module with a distal end and a proximal end;
   a cannula tunnel formed in the needle cannula module, wherein the cannula tunnel extends from the distal end to the proximal end of the needle cannula module and wherein the proximal end of the needle cannula module is fixed to the distal end of the syringe body;
   a needle cannula with a distal end and a proximal end, wherein a needle cannula flange is formed on the proximal end of the needle cannula;
   a plunger module with a distal end and a proximal end, wherein the plunger module is moveably disposed in the syringe body for pushing fluid in the syringe body for explosion out of the needle cannula;
   a barrier cannula with a distal end and a proximal end, wherein the barrier cannula is connected to the proximal end of the needle cannula module and wherein the barrier cannula has cannula formed there through permitting fluid communication between the syringe body and the needle cannula;
   an annular cone shear and cutter head with a distal end and a proximal end, wherein the proximal end is fixed to the distal end of the plunger module and wherein the distal end is formed into a cutting edge for shearing and cutting;
   a plunger barrier with a distal end and a proximal end, wherein the proximal end of the plunger barrier is supported on the cutting edge on the distal end of the annular cone shear and cutter head, wherein the distal end of the plunger barrier forms a fluid tight seal with the inside surface of the syringe body, wherein thrusting the plunger in a distal direction causes the cutting edge to push the plunger barrier in the distal direction, and then thrusts the distal end of the plunger barrier against the proximal end of the barrier cannula, causing the distal end of said annular cone shear and cutter head to cut the plunger barrier and the barrier cannula to free the needle cannula, wherein the needle cannula is moveable through the barrier cannula, through the plunger barrier and through the annular cone shear and cutter head and into the plunger module.

2. The syringe of claim 1 wherein the needle cannula module further comprising, a biasing means in the cannula tunnel for urging the needle cannula into the plunger module upon cutting or shearing of the barrier cannula and the plunger barrier.

3. The syringe of claim 2 wherein the needle cannula module of claim 2 further comprising of an annular spring guide with a distal end and a proximal end wherein a cannula flat is formed on said distal end of said spring guide and said biasing means including a spring with a distal end and a proximal end wherein said distal end of said spring is abutting and urged against said cannula flat.

4. The needle cannula module of claim 3 wherein said spring is movable into said plunger module.

5. The needle cannula module of claim 3 further comprising an annular recess between the needle cannula module and the syringe body wherein the outer periphery of the barrier cannula project outwardly and is disposed in said annular recess.

6. The syringe of claim 1 wherein the needle cannula module has an interior circumferential channel, the annular shear and cutter head having a distal cutting edge sized and configured for receipt within said interior circumferential channel and for facilitating shearing or cutting or breaking of the plunger barrier and the barrier cannula by said annular shear and cutter head.

7. The syringe of claim 1 wherein the barrier cannula has a needle cannula module gasket disposed between said proximal end of the needle cannula module and the distal end of said syringe body.

8. The syringe of claim 1 wherein said barrier cannula has a barrier recess formed in said proximal end thereof and said plunger barrier has a plunger projecting portion projecting from said distal end thereof, the barrier recess and said plunger projecting portion each having corresponding shapes for mating abutment of the plunger barrier against the barrier cannula so that fluid flow to said needle cannula is closed off upon said abutment wherein the plunger is movable to urge said plunger barrier into abutment against the barrier cannula.

9. The syringe of claim 1 wherein the plunger barrier is further comprised of, a plunger gasket projecting from the plunger barrier for sealing off a space between said inside surface of said syringe body and the outside surface of said annular shear and cutter head, thereby preventing fluid in the syringe body from flowing into said space.

10. The syringe of claim 1 wherein the plunger barrier is deformable against the barrier cannula when pushed there against.

11. The syringe of claim 1 further comprising, a circumferential latch for locking the annular cone shear and cutter head to a slip over retainer after said annular cone shear and cutter head has cut said plunger barrier and said barrier cannula.

12. The syringe of claim 11 wherein said circumferential latch comprising; a needle cannula within said needle module defined by a projecting hollow cylindrical body encompassing a portion of said needle cannula, a circumferential latch on an exterior surface of a cannula hub and a slip over retainer on the annular shear and cutter head positioned for engaging said circumferential latch of the cannula hub to lock the annular shear and cutter head and the plunger module connected thereto to the cannula hub thus preventing movement of said plunger module.

13. The syringe of claim 1 further comprising second locking means for locking the plunger module to the syringe body.

14. The syringe of claim 13 wherein the second locking means comprises the syringe body with a finger flat at the proximal end of said syringe body, and a plunger lock at the proximal end of the plunger module wherein said plunger lock is moveable to engage said finger flat to lock said plunger module to said syringe body.

15. The syringe of claim 1 further comprising the distal end of the syringe body having interior threads, the proximal end of the needle cannula module having exterior threads for threadedly mating with the interior threads of the distal end of the syringe body to connect the needle cannula module to the syringe body.

16. A syringe, comprising:
a syringe body with a distal end, a proximal end and a syringe channel there through from the distal end to the proximal end;
a needle cannula module having a distal end, a proximal end and a cannula channel extending from the distal end to the proximal end, wherein the cannula channel further is formed into an annular spring guide;
a needle cannula having a distal end and a proximal end, wherein the distal end projects from and extends beyond the needle cannula module, and the proximal end is within the annular spring guide, and wherein the needle cannula has a channel there through from the distal end to the proximal end and a needle cannula flange formed at the proximal end;
a plunger module with a distal end, a proximal end, and a plunger channel there through, wherein the distal end is movably disposed in the syringe channel for pushing fluid in the syringe channel to and through the needle cannula for expulsion from the distal end of the needle cannula;
a barrier cannula connected to the needle cannula module and extending across the proximal end, wherein the needle flange is abutting the barrier cannula, the barrier cannula initially preventing the needle cannula from moving into the syringe body, the barrier cannula having a cannula or channel there through permitting fluid communication between the syringe channel and the needle channel;
an annular shear and cutter head at the distal end of the plunger module having a distal end, a proximal end, and a shear and cutter head channel formed there through from the distal end to the proximal end;
a plunger barrier adjacent to the shear and cutter and initially closing off the distal end of the plunger module wherein the plunger barrier is movable with the annular shear and cutter head within the syringe body, wherein the annular shear and cutter head is movable by moving the plunger module to cut the plunger barrier and to shear the barrier cannula to free the needle cannula so that the needle cannula is movable through the annular shear and cutter head and into the plunger module;
a circumferential latch and a slip over retainer for engaging the circumferential latch, wherein the circumferential latch and the slip over retainer lock the cannula shear and cutter head to the needle cannula module after the annular shear and cutter head has sheared or cut the plunger barrier and the barrier cannula, and wherein the slip over retainer is a notch on an inside surface of the annular shear and cutter head.

17. The syringe of claim 16 further comprising a biasing means such as a spring in the cannula channel for urging the needle cannula into the plunger channel upon breaking of the barrier cannula and the plunger barrier.

18. A syringe, comprising:
a syringe body with a distal end, a proximal end, and a syringe channel there through from the distal end to the proximal end;
a needle cannula module having a distal end, a proximal end and a cannula channel extending from the distal end to the proximal end;
a needle cannula having a distal end and a proximal end, wherein the distal end projects from and extends beyond the distal end of the needle cannula module and the proximal end is within the cannula channel, and wherein a cannula flange is formed at the proximal end of the needle cannula;
an inverted cutter head with a distal end and a sharp edge on a proximal end, wherein the distal end is fixed to the needle cannula module and the proximal end is near the proximal end of the needle cannula module;
a barrier cannula with a distal end, a proximal end, an outer periphery and a cannula that extends from the distal end to the proximal end of the barrier cannula wherein the outer periphery of the barrier cannula is fixed to the distal end of the needle cannula module, and wherein the distal end of the barrier cannula is located proximally from the proximal end of the inverted cutter head;
a plunger module with a distal end, a proximal end, and a plunger channel there through, wherein the distal end is movably disposed in the syringe channel for pushing fluid in the syringe channel to and through the needle cannula for expulsion from the distal end of the needle cannula;
a plunger barrier fixed to the distal end of the plunger module, wherein the plunger barrier is moveable with the distal end of the plunger module, wherein the plunger module is urged towards the inverted cutter head, wherein the plunger barrier is urged into the barrier cannula further urging the cannula barrier into the sharp edge of the inverted cutter head, and wherein the inverted sharp edge of the inverted cutter head further cuts or shears a section out of the barrier cannula and then cuts or shears a section out the plunger barrier forming a tunnel in the barrier cannula and the plunger barrier, wherein the needle cannula flange and the needle cannula is released and the needle cannula is allowed to retract into the plunger tunnel.

19. The syringe of claim 18 wherein said inverted cutter head has a triangular cross-section.

20. The syringe of claim 18 wherein an annular cutter head foundation is formed at said proximal end of needle cannula module.

21. The syringe of claim 20 wherein a cutter head flange is formed on said cutter head foundation and wherein said cutter head flange further supports said inverted cutter head.

22. The syringe of claim 18 wherein said syringe is further comprised of;
- a cutter head foundation extending from said proximal end of said needle cannula module;
- a cutter head flange formed on said annular cutter head foundation wherein said cutter head flange further supports said inverted cutter head;
- a plunger barrier support flange formed on said distal end of said plunger module wherein said plunger barrier support flange also forms a cannula passage to allow said needle cannula, said needle cannula flange, part of said plunger barrier and part of said cannula barrier to enter said plunger tunnel in said plunger module.

23. The syringe of claim 22 wherein said plunger barrier support flange will move past said inverted cutter head and said cutter head flange and latch on to the cutter head flange thereby looking said plunger module to said needle cannula module.

24. The syringe of claim 18 wherein a partial biased spring is disposed in said cannula channel formed in said needle cannula module and wherein said partial biased spring has a distal end and a proximal end and wherein said distal end is urged on said cannula flat and wherein said proximal end is urged on said needle cannula flange and wherein said partial biased spring is partially compressed to allow the partial biased spring to be further compressed when said plunger module is urging said plunger barrier and said barrier cannula into said inverted cutter head further exposing said sharp edge of said inverted cutter head thereby allowing said sharp edge of said inverted cutter head to cut said plunger barrier and said barrier cannula in a more efficient manner and wherein said partial biased spring further urges said needle cannula and said needle cannula flange into said plunger tunnel.

25. The syringe of claim 18 wherein said needle cannula falls into said plunger channel with aid of gravity or by shaking said syringe after the plunger barrier and the barrier cannula have been cut.

* * * * *